(12) United States Patent
Yarden et al.

(10) Patent No.: US 7,939,072 B2
(45) Date of Patent: May 10, 2011

(54) ANTI-EGFR ANTIBODIES WITH AN IMPROVED ANTI-TUMOR ACTIVITY AND COMPOSITIONS AND ARTICLES OF MANUFACTURE COMPRISING SAME

(75) Inventors: Yosef Yarden, Rechovot (IL); Michael Sela, Rechovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 12/320,207

(22) Filed: Jan. 21, 2009

(65) Prior Publication Data

US 2009/0155288 A1 Jun. 18, 2009

Related U.S. Application Data

(62) Division of application No. 11/342,615, filed on Jan. 31, 2006, now Pat. No. 7,498,142.

(51) Int. Cl.
*A61K 39/395* (2006.01)
(52) U.S. Cl. .................................................. 424/138.1
(58) Field of Classification Search .................. None
See application file for complete search history.

(56) References Cited

U.S. PATENT DOCUMENTS

| 5,587,458 | A | 12/1996 | King et al. |
| 7,498,142 | B2 | 3/2009 | Yarden et al. |
| 2003/0086924 | A1 | 5/2003 | Sliwkowski |
| 2003/0170235 | A1 | 9/2003 | Cohen |
| 2007/0178102 | A1 | 8/2007 | Yarden et al. |

OTHER PUBLICATIONS

Friedman et al (PNAS, epub Jan. 31, 2005, 102:1915-1920).*
Stratagene catalog 1988, p. 39.*
Johnstone and Thorpe (Immunochemistry in Practice, 2nd Ed., 1987, Blackwell Scientific Publications, Oxford, pp. 49-50).*
Official Action Dated Nov. 1, 2007 From the US Patent and Trademark Office Re.: U.S. Appl. No. 11/342,615.
Official Action Dated Apr. 11, 2007 From the US Patent and Trademark Office Re.: U.S. Appl. No. 11/342,615.
Notice of Allowance Dated Oct. 7, 2008 From the US Patent Office Re.: U.S. Appl. No. 11/342,615.
Official Action Dated Sep. 17, 2009 From the US Patent and Trademark Office Re.: U.S. Appl. No. 12/320,207.
Official Action Dated May 22, 2008 From the US Patent Office Re.: U.S. Appl. No. 11/342,615.
Official Action Dated Dec. 27, 2006 From the US Patent Office Re.: U.S. Appl. No. 11/342,615.
Response Dated Oct. 19, 2009 of Official Action to Sep. 17, 2009 From the US Patent and Trademark Office Re.: U.S. Appl. No. 12/320,207.
Chen et al. "An Immunological Approach Reveals Biological Differences Between the Two NDF/Heregulin Receptors, ErbB-3 and ErbB-4", The Journal of Biological Chemistry, 271(13): 7620-7629, 1996.
Drebin et al. Monoclonal Antibodies Reactive With Distinct Domains of the Neu Oncogene-Encoded P185 Molecule Exert Synergistic Anti-Tumor Effects In Vivo, Oncogene, 2: 273-277, 1988.
Friedman et al. "Synergistic Down-Regulation of Receptor Tyrosine Kinases by Combinations of mAbs: Implications for Cancer Immunotherapy", PNAS, 102(6): 1915-1920, 2005.
Hurwitz et al. "Suppression and Promotion of Tumor Growth by Monoclonal Antibodies to ErbB-2 Differentially Correlate With Cellular Uptake", Proc. Natl. Acad. Sci. USA, 92(8): 3353-3357, 1995.
Kasprzyk "A Therapy of An Animal Model of Human Gastric Cancer Using A Combination of Anti-ErbB-2 Monoclonal Antibodies", Cancer Research, 52: 2771-2776, 1992.
Kipriyanov et al. "Recent Advances in the Generation of Bispecific Antibodies for Tumor Immunotherapy", Current Opinion in Drug Discovery & Development, 7(2): 233-242, 2004.
Klapper et al. "A Subclass of Tumor-Inhibitory Monoclonal Antibodies to ErbB-2/HER2 Blocks Crosstalk With Growth Factor Receptors", Oncogene, 14: 2099-2109, 1997.
Klapper et al. "Tumor-Inhibitory Antibodies to HER-2/ErbB-2 May Act by Recruiting c-Cbl and Enhancing Ubiquitination of HER-2[1]", Cancer Research, 60: 3384-3388, 2000.
Merimsky et al. "Induction Chemotherapy for Bone Sarcoma in Adults: Correlation of Results With ErbB-4 Expression", Oncology Reports, 10: 1593-1599, 2003.
Nahta et al. "The HER-2-Targeting Antibodies Trastuzumab and Pertuzumab Synergistically Inhibit the Survival of Breast Cancer Cells", Cancer Research, 64: 2343-2346, 2004.
Persson et al. "[177Lu]Pertuzumab: Experimental Studies on targeting of HER-2 Positive Tumour Cells", European Journal of Nuclear Medicine and Molecular Imaging, 32(12): 1457-1462, 2005.
Slamon et al. "Studies of the HER-2/Neu Proto-Oncogene in Human Breast and Ovarian Cancer", Science, 244(4905): 707-712, 1989.
Spiridon et al. "Targeting Multiple Her-2 Epitopes With Monoclonal Antibodies Results in Improved Antigrowth \Activity of A Human Breast Cancer Cell Line In Vitro and In Vivo", Clinical Cancer Research, 8: 1720-1730, 2002.
Tokunaga et al. "Trastuzumab and Breast Cancer: Developments and Current Status", Int. J. Clin. Oncol., 11(3): 199-208, 2006, Abstract.
Yarden "Biology of HER2 and Its Importance in Breast Cancer", Oncology, 61(suppl 2): 1-13, 2001.

* cited by examiner

*Primary Examiner* — Laura B Goddard

(57) ABSTRACT

A method of identifying a combination of antibodies with a combined improved anti tumor activity is provided. The method comprising identifying at least two anti RTK antibodies capable of inducing synergistic endocytosis of the RTK in a cell expressing the RTK, thereby identifying the combination of antibodies with the combined improved anti-tumor activity.

2 Claims, 6 Drawing Sheets
(1 of 6 Drawing Sheet(s) Filed in Color)

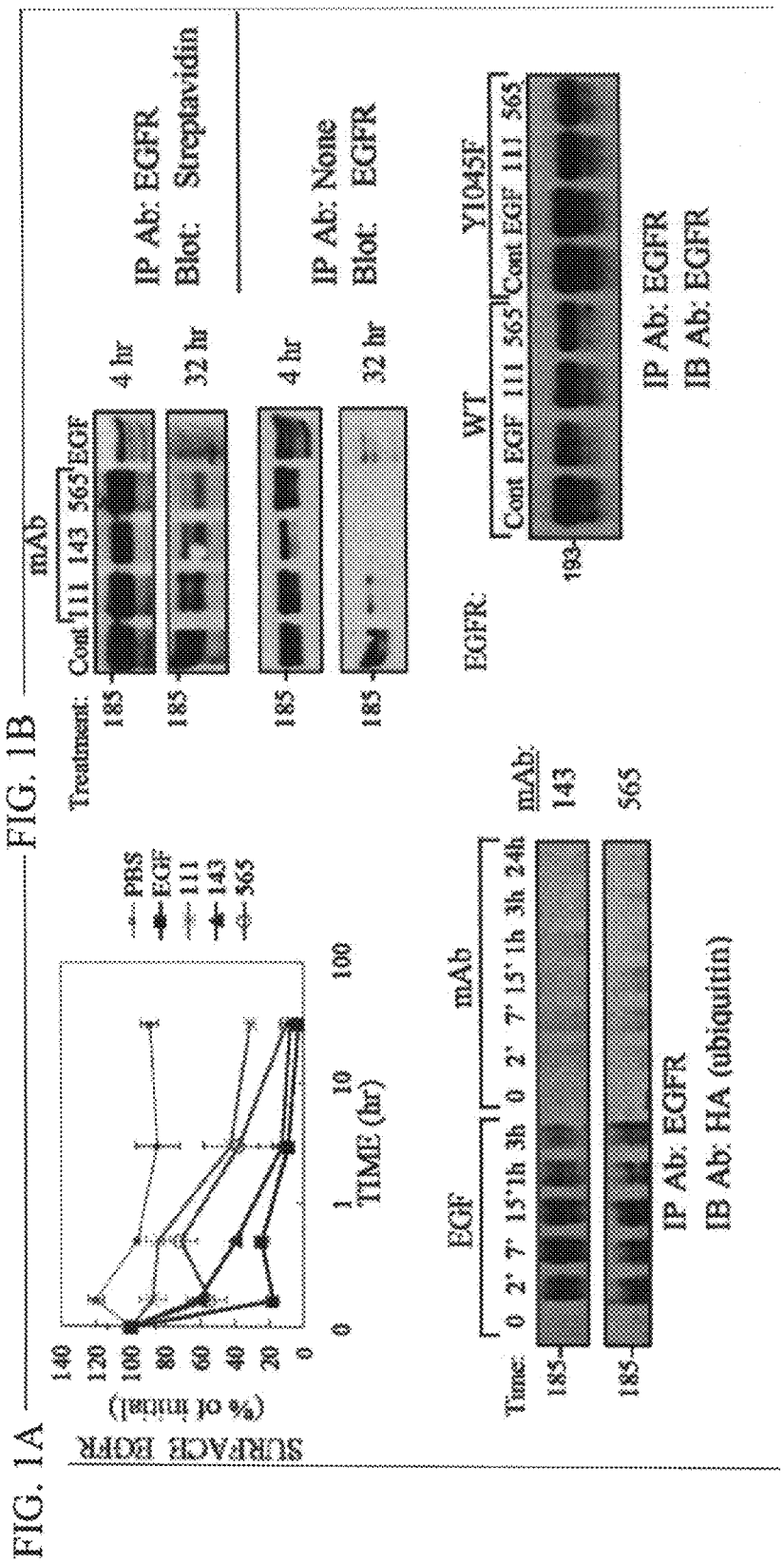
FIGS. 1A-D

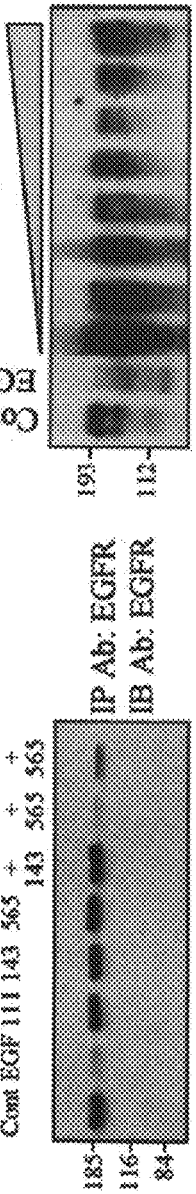
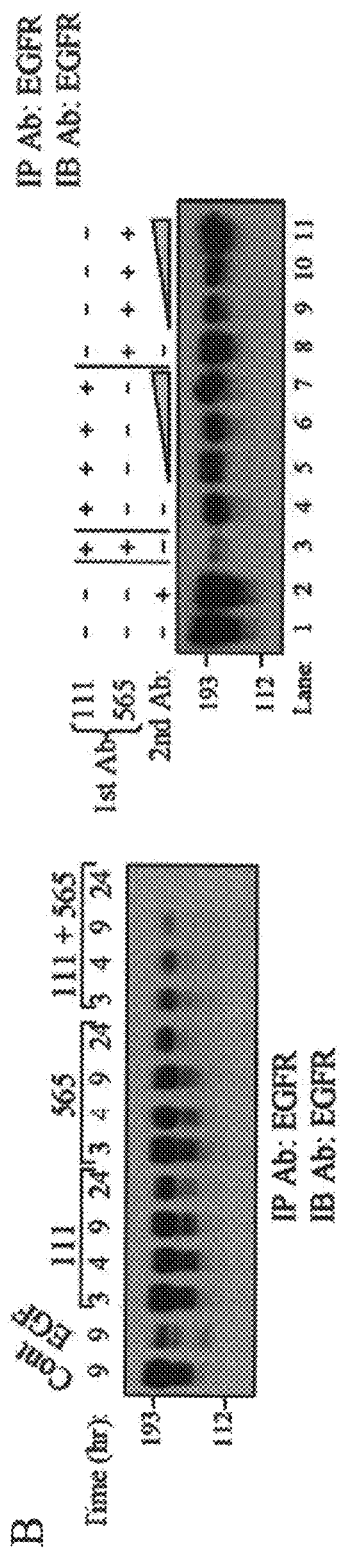
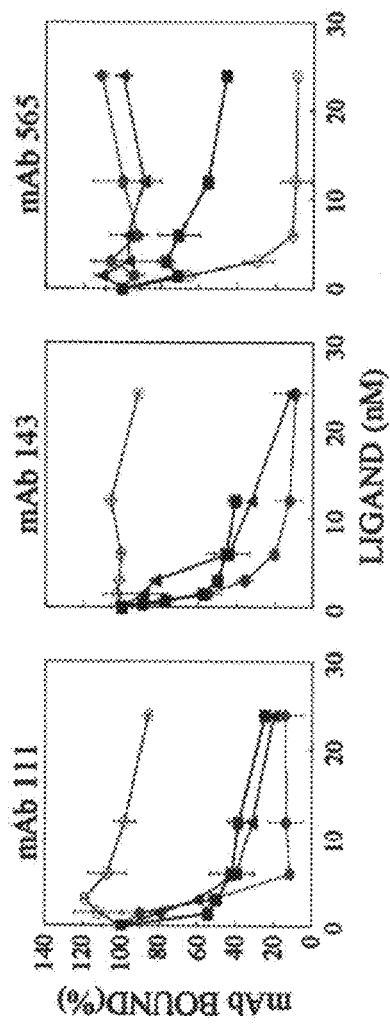
FIGS. 2A-D

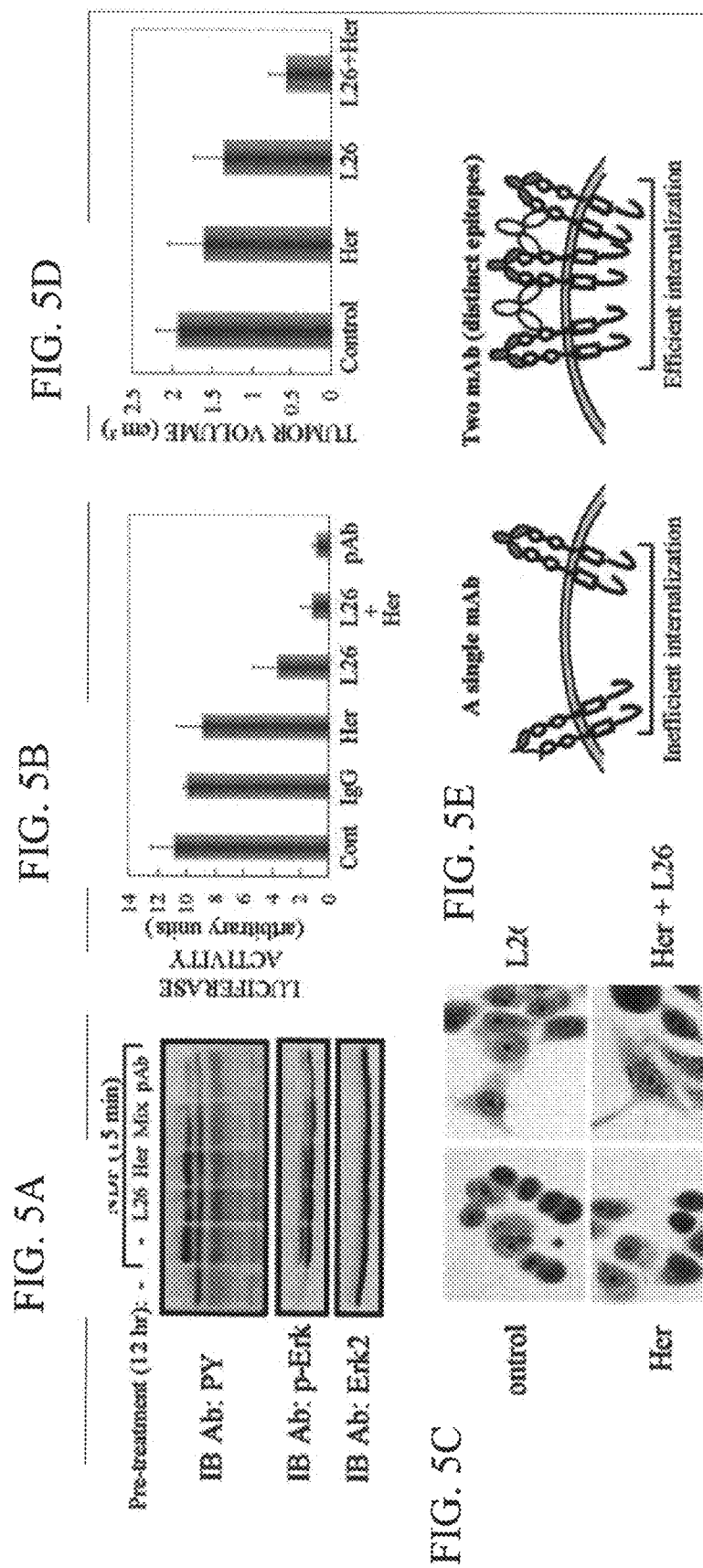
FIGS. 5A-E

ANTI-EGFR ANTIBODIES WITH AN IMPROVED ANTI-TUMOR ACTIVITY AND COMPOSITIONS AND ARTICLES OF MANUFACTURE COMPRISING SAME

RELATED APPLICATIONS

This application is a divisional of U.S. patent application Ser. No. 11/342,615, filed on Jan. 31, 2006, now U.S. Pat. No. 7,498,142.

STATEMENT OF GOVERNMENT INTEREST

This invention was made in part by the government support under contract No. R01 CA072981 awarded by the National Cancer Institute. The United States Government has certain rights in the invention.

FIELD AND BACKGROUND OF THE INVENTION

The present invention relates to methods of identifying combinations of antibodies with a combined improved anti tumor activity. The present invention further relates to pharmaceutical compositions comprising such antibodies which can be used for therapy, such as for cancer therapy.

Receptor tyrosine kinases (RTK) constitute a large family of cell surface proteins that act as scaffolding mediators and molecular switches in many signal transduction pathways, affecting cell growth, proliferation, differentiation, survival and migration. Receptors with tyrosine kinase activity share a similar molecular topology, essentially an extracellular ligand binding domain, a membrane spanning hydrophobic domain, and a cytoplasmic domain that comprises a highly conserved tyrosine kinase catalytic domain. RTKs comprise an array of extracellular domains that bind a variety of growth factors. Characteristically, the extracellular domains are comprised of one or more identifiable structural motifs, including cysteine-rich regions, fibronectin III-like domains, immunoglobulin-like domains, EGF-like domains, cadherin-like domains, kringle-like domains, Factor VIII-like domains, glycine-rich regions, leucine-rich regions, acidic regions and discoidin-like domains. Although diverse, RTK activation, initiation of signal transduction, and signal termination follow the same universal model (Yarden, Y., et al., Ann. Rev. Biochem 57:443-478, 1988; Ullrich, A. and Schlessinger, J., Cell 81, 203-212, 1990).

RTKs play a central role in the onset and progression of human disease, particularly cancer, such as breast, colon, lung and prostate cancers. As such, RTKs are preferred targets for the design and configuration of various therapeutic modalities.

Following ligand binding and onset of signaling, ligand-bound receptors are down regulated by removal from the cell surface. This universal mode of down regulation involves ligand-induced internalization by means of endocytosis, primarily via clathrin-coated pits, followed by receptor degradation. RTKs can also be endocytosed from invaginations other than clathrin-coated pits (e.g., caveoli), but the significance of this alternative internalization in RTK downregulation is not yet known. Deregulation of RTK endocytosis is a recurring factor in cancer progenesis (Peschard and Park, Cancer Cell 3: 519-523, 2003; Bache, K. G. et al., EMBO 23: 2707-2712, 2004). Indeed, more than 30 RTKs were found to be associated with cancer, through defective down regulation alone (Blume-Jensen, P. and Hunter, T. Nature 411: 355-365, 2001). Following this and other lines of research, a broad range of RTK inhibitors are being developed for use as anti-cancer agents or therapeutic agents against other RTK related diseases such as epidermal hyperplasia. RTK inhibitors e.g., epidermal growth factor receptor (EGFR), vascular endothelial growth factor receptor (VEGFR), platelet-derived growth factor receptor (PDGFR), Fms-like tyrosine kinase (Flt-3) are constantly being developed [for examples see U.S. Pat. Nos. 6,900,186 (e.g., RTK down regulation for the treatment of skin disorders); 6,399,063 (e.g., down regulation of ErbB-2 with mAb); 5,837,523 (kinase deficient Neu mutants); 5,705,157 (e.g., mAb against EGFR increase receptor down regulation).

While the invention will be described herein in more detail with respect to the ErbB family of RTKs, it is to be understood that the invention is applicable for all RTKs.

The ErbB family of receptor tyrosine kinases, which includes the prototype, epidermal growth factor receptor (EGFR), also termed ErbB-1, and the related proteins ErbB-2, ErbB-3 and ErbB-4 is widely known and researched. The four known members of the ErbB family and their multiple ligand molecules form a layered signaling network, which is implicated in human cancer. Thus, overexpression of ErbB-1/EGF receptor (EGFR) as well as ErbB-2 has been correlated with poor prognosis in various human malignancies. Specifically, deletion mutants of EGFR exist in brain tumors and point mutations have recently been reported in lung cancer. By contrast, ErbB-2/HER2 is rarely mutated in solid tumors. Instead, the ErbB-2 gene is frequently amplified in breast, ovarian, and lung cancer.

Because of their oncogenic potential and accessibility, ErbB proteins have emerged as attractive targets for pharmaceutical interventions. One major strategy involves the use of mAbs. Early studies uncovered the tumor-inhibitory potential of mAbs directed at ErbB-1 and ErbB-2, and later studies indicated that anti-ErbB mAbs are effective when combined with various chemotherapeutic agents. Indeed, the clinical benefit of combining mAbs with certain chemotherapeutic agents was notable, and led to the approval of mAbs to ErbB-2 (Herceptin) and EGFR(C225/Cetuximab) for the treatment of breast and colorectal cancer, respectively. Other antibodies now in clinical trials include MDX-210 (phase II, Medares), tgDCC-Eia (phase II, Targeted Genetics) and 2C4 (phase I, Genentech) (Zhang H. et al., Cancer Biol. Therap., 2: S122-S126, 2003). Unfortunately, the therapeutic efficacy of these and other RTK inhibitors is limited and varies dramatically between patients. There is thus a need to elucidate the mechanism underlying antibody mediated therapy.

Two types of mechanisms have been implicated in ErbB-directed immunotherapy. The first involves mAb-mediated recruitment of natural killer cells through the Fc-γ activation receptors of these immune effector cells to the tumor site. The second type of mechanism relates to intrinsic mAb activities, which include blockade of ligand binding or receptor pharmaceutical composition comprising as an active ingredient at least two anti RTK antibodies capable of inducing synergistic endocytosis of the RTK in a cell expressing the RTK.

According to still another aspect of the present invention there is provided a method of treating cancer in a subject, the method comprising administering to a subject in need thereof a therapeutically effective amount of at least two anti RTK antibodies capable of inducing synergistic endocytosis of the RTK in a cell expressing the RTK, thereby treating cancer in the subject.

According to further features in preferred embodiments of the invention described below, the at least two antibodies are directed to distinct extracellular epitopes of the RTK.

According to still further features in the described preferred embodiments each of the at least two antibodies bind the RTK with an affinity of at least 200 nM.

According to still further features in the described preferred embodiments the at least two antibodies bind the RTK with a similar affinity.

According to still further features in the described preferred embodiments the RTK is an ErbB protein.

According to still further features in the described preferred embodiments the ErbB protein is selected from the group consisting of ErbB-1, ErbB-2, ErbB-3 and ErbB-4.

According to still further features in the described preferred embodiments the RTK is selected from the group consisting of c-met, PDGFR, ErbB, VEGFR, EphR, FGFR, INSR and AXL.

According to still further features in the described preferred embodiments the at least two antibodies comprise a recombinant antibody.

According to still further features in the described preferred embodiments the recombinant antibody is a bispecific antibody or a single chain antibody.

According to still further features in the described preferred embodiments the at least two antibodies comprise a monoclonal antibody.

According to still further features in the described preferred embodiments the at least two antibodies comprise a polyclonal antibody.

According to still further features in the described preferred embodiments the at least two antibodies comprise a humanized antibody.

According to still further features in the described preferred embodiments the at least two antibodies comprise an antibody fragment.

According to still further features in the described preferred embodiments the at least two antibodies comprise at least a bivalent antibody.

According to still further features in the described preferred embodiments the endocytosis is c-Cbl independent.

According to still further features in the described preferred embodiments the endocytosis is ubiquitylation independent.

According to still further features in the described preferred embodiments the method further comprising subjecting the subject to a therapy selected from the group consisting of a radiotherapy and a chemotherapy.

The present invention successfully addresses the shortcomings of the presently known configurations by providing methods of identifying combinations of antibodies with a combined improved anti tumor activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 3B:
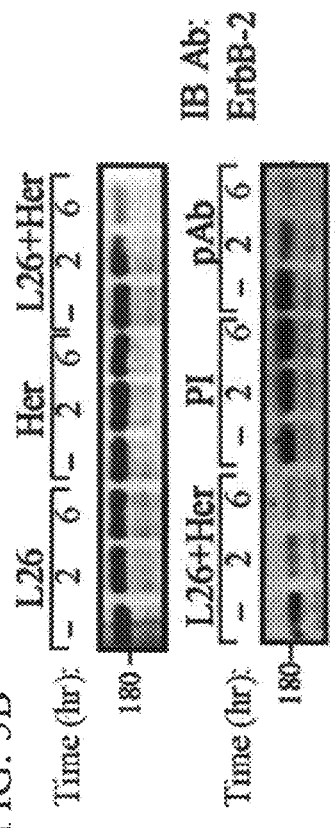
Figure 3D:
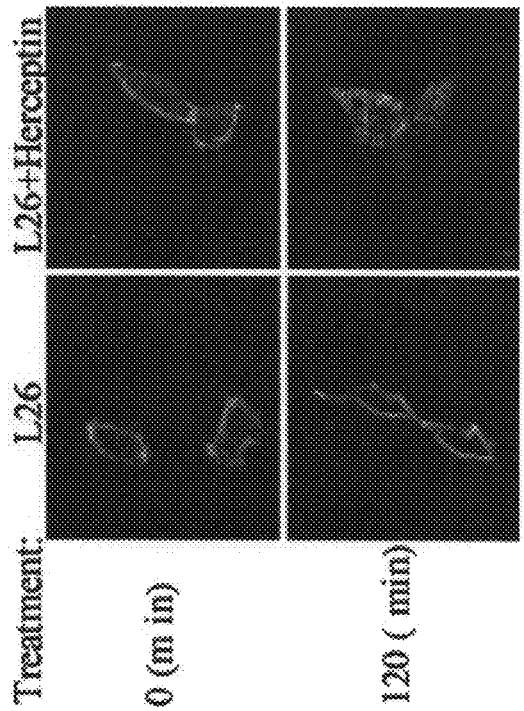
Figure 3A:
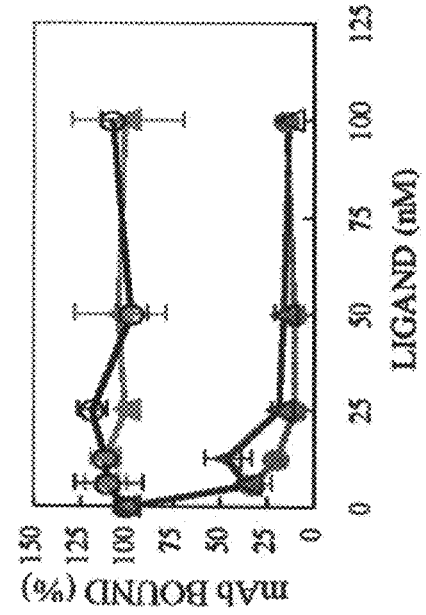
Figure 3C:
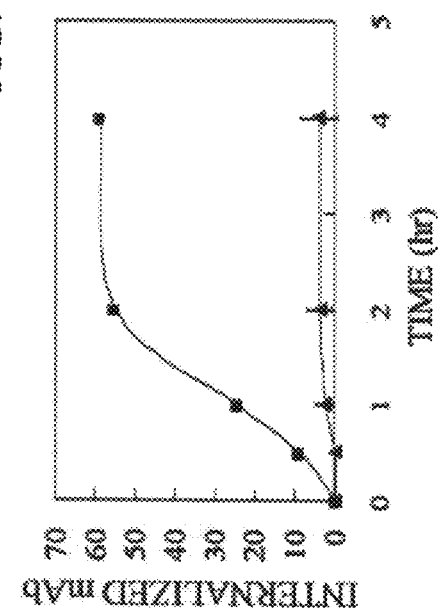
Figure 4C:
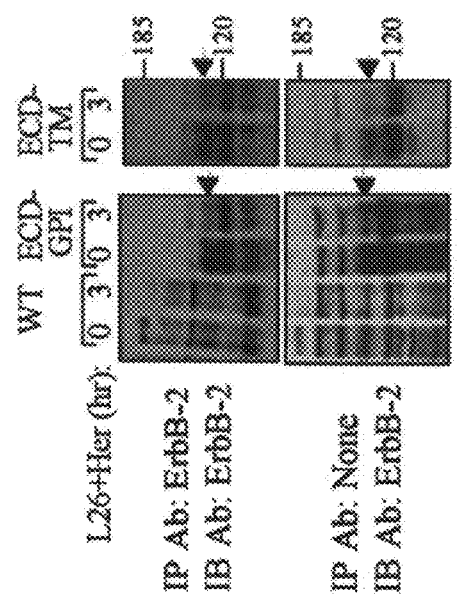
Figure 4B:
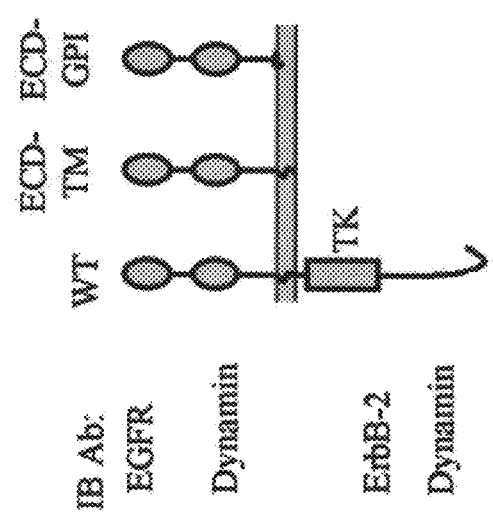
Figure 4A:
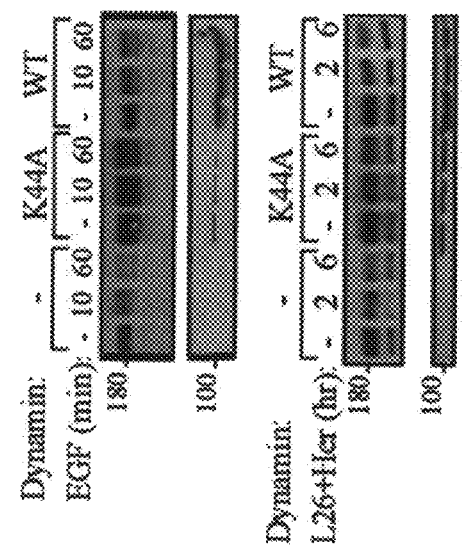
Figure 6A:
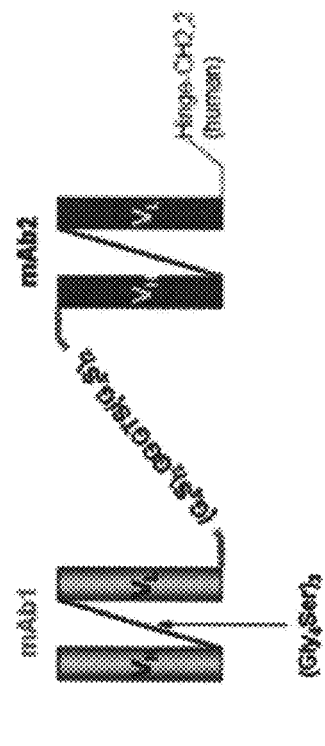
Figure 6B:
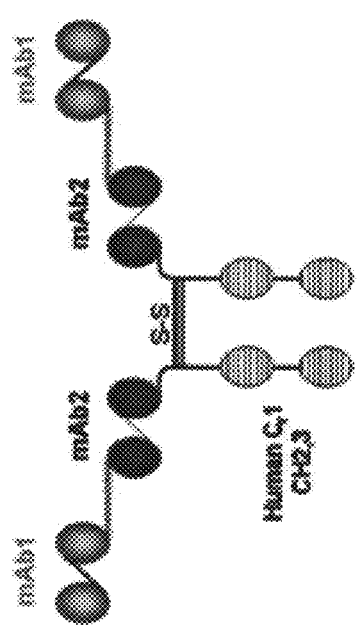

FIGS. 1a-d depict distinct endocytic behavior of EGFR treated with EGF and mAbs. FIG. 1a is a graph depicting cell-surface EGFR following treatment with EGF and the indicated antibodies for various time periods. KB cells were treated with EGF (100 ng/ml) or mAbs (20 µg/ml) at 37° C. for various time intervals. The cells were then washed and acid-stripped, and levels of surface receptor were determined (average±SD) using radiolabeled EGF; FIG. 1b is an immunoblot showing surface expression of EGFR in cells treated for 4 or 32 hours with anti EGFR antibodies, EGF or no treatment, as determined by surface biotinylation. KB cells were treated as indicated and washed as in FIG. 1a. Cells were either subjected to surface biotinylation followed by lysis and immunoprecipitation and blotting with streptavidin-horseradish peroxidase (Upper panel) or directly lysed and immunoblotted with anti-EGFR Ab (Lower panel); FIG. 1c is an immunoblot showing that down-regulation of EGFR by mAbs is independent of receptor ubiquitilation. CHO cells transiently expressing EGFR, c-Cbl and hemagglutinin (HA)-ubiquitin were incubated with EGF (100 ng/ml) or the indicated mAbs (20 µg/ml) for various intervals. Cells were lysed and subjected to immunoprecipitation with anti EGFR and immunoblotting with anti HA. FIG. 1d is an immunoblot showing that antibody-mediated EGFR endocytosis is c-Cbl independent. CHO cells were co-transfected with WT- or Y1045F-EGFR (which cannot directly recruit c-Cbl), along with c-Cbl. Transfected cells were incubated with EGF (100 ng/ml; 1 h), saline, or the indicated mAbs (10 µg/ml; 18 h). Cells were washed for removal of bound ligands, lysed, and subjected to immunoprecipitation and immunoblotting with anti EGFR;

FIGS. 2a-d depict better down regulation of EGFR following treatment with combinations of anti-receptor mAbs as compared to treatment with individual mAbs. FIG. 2a is an immunoblot showing surface expression of EGFR in KB cells treated for 13 hours with individual anti EGFR mAbs, a combination of antibodies (total: 20 µg/ml), EGF (100 ng/ml) or no treatment. Following incubation, cells were stripped of bound ligands, lysed and extracts were subjected to immunoprecipitation and immunoblotting with anti EGFR; FIG. 2b is an immunoblot showing surface expression of EGFR in KB cells after incubation for various time intervals with anti EGFR antibodies, a combination of antibodies (total: 20 µg/ml), EGF (100 ng/ml) or no treatment. Extracts were analyzed as in FIG. 2a. FIG. 2c shows three graphs depicting cross competition analyses between three mAb. KB cells were treated for 1 h at 4° C. with mAbs 111 (closed circle), 143 (closed triangle), 565 (open circle), or EGF (closed square). The indicated radiolabeled mAbs (8 nM) were then added, and the cells were incubated for an additional 15 min before determination of radioactivity. The graphs depict the percent of bound radiolabeled antibody as it is affected by the incubation with other antibodies, or EGF; FIG. 2d is an immunoblot showing rate of receptor down-regulation is proportional to the size of Ab-receptor lattice. The upper panel is an immunoblot showing surface expression of EGFR in cells treated for 18 h with saline (Cont) or EGF (100 ng/ml), or co-treated with mAbs 111 (10 μg/ml) and increasing amounts (2.5-20 μg/ml) of 565. The lower panel is an immunoblot showing surface expression of EGFR in KB cells treated with saline, EGF (100 ng/ml), or the indicated mAbs (total: 10 μg/ml) for 3 h at 4° C., followed by a change of medium of all cells (except lane 3) to a fresh medium containing a goat anti-mouse IgG (second Ab: either 40 or 10, 20, and 40 μg/ml). Cells were incubated for additional 18 h at 37° C., washed, lysed, and subjected to immunoprecipitation followed by immunoblotting with anti-EGFR;

FIGS. 3a-d depict better down regulation of ErbB-2 treated with combinations of antibodies as compared to treatment with individual mAbs. FIG. 3a is a graph depicting cross competition analyses between 2 mAbs. SKBR-3 cells were treated with various concentrations of the mAb L26 (circles) or Herceptin™ (triangles) at 4° C. Radiolabeled mAb L26 (8 nM; closed symbols) or Herceptin™ (open symbols) were then added, and the cells were incubated for 15 min. After washing, radioactivity was measured and expressed as average percent of bound antibody±SD. FIG. 3b an immunoblot showing surface expression of ErbB-2 is lower in cells treated with a combination of mAb. HEK-293T cells (Upper panel) ectopically expressing ErbB-2 or T47D cells (Lower panel) were treated with L26 and/or Herceptin™ (Her; total: 20 μg/ml) or preimmune Abs (PI) or pAb, at 37° C. for the indicated time intervals. Cells were then washed lyzed and subjected to immunoblotting with anti-ErbB-2. FIG. 3c is a graph showing the percent of internalized 4D5 (a parental form of Herceptin) is higher when it is used in treatment together with L26. SKBR-3 cells were treated with fluorescein-labeled 4D5-mAb (10 μg/ml) at 37° C. for the indicated time intervals in the absence (closed rectangle) or presence (closed square) of L26. Thereafter, cells were washed and acid-stripped, and internalized 4D5 was determined by using a cell sorter. FIG. 3d is a confocal microscopy photograph of CB2 cells that were incubated with a mixture of L26 and Herceptin™ (20 μg/ml each) or L26 alone (40 μg/ml) at 37° C. for the indicated time periods. Thereafter, cells were washed, fixed, and permeabilized, and ErbB-2 was detected by using confocal microscopy with a Cy3-conjugated anti-mouse IgG;

FIGS. 4a-c depict down-regulation of ErbB-2 by combinations of mAbs is dynamin-dependent but requires no cytoplasmic or transmembrane portions of ErbB-2. FIG. 4a is an immunoblot showing that down regulation of EGFR and ErbB-2 is dynamin dependent. HEK-293T cells were cotransfected either with plasmids encoding EGFR (Upper panel) or ErbB-2 (Lower panel), along with plasmids encoding c-Cbl and dynamin (WT or K44A—a dominant negative form of dynamin which blocks EGF endocytosis). After 48 h, cells were treated with EGF (100 ng/ml) or a combination of L26 and Herceptin™ (Her; total: 20 μg/ml). Cells were then lyzed immunoblotted with anti-EGFR (Upper panel) or anti-ErbB-2 (Lower panel), and anti-Dynamin Ab; FIG. 4b is a diagram showing the ErbB-2 molecules analyzed. The diagram shows either WT, a mutant lacking the cytoplasmic domain (ECD-TM), or the full ectodomain fused to a GPI-attachment signal (ECD-GPI). FIG. 4c is an immunoblot showing that no cytoplasmic or transmembrane motifs of ErbB-2 are necessary for mAb-induced internalization and degradation. CHO cells were transfected with either WT, ECD-GPI or ECD-TM mutant forms of ErbB-2. Cells were treated for 0 or 3 h with a mixture of mAbs L26 and Herceptin™ (5 μg/ml each), and washed to remove bound ligands. Cells were then either subjected to lysis, immunoprecipitation and blotting with anti-ErbB-2 Ab (Upper panel), or were directly lysed and immunoblotted with anti-ErbB-2 Ab. The lower panel shows that when electrophorased, the two mutants display two bands corresponding to 120 and 135 kDa, but experimental data has shown that only the 135 kDa species had reached the plasma membrane and underwent down-regulation upon treatment with mAb (data not shown). In accordance, only the 135 kDa surface-localized forms of ECD-GPI and ECD-TM (arrows) were affected by mAbs;

FIGS. 5a-e depict inhibition of growth factor signaling, promotion of differentiation, and reduction of tumor growth by combinations of anti-ErbB-2 Abs. FIG. 5a is an immunoblot showing that NDF mediated ErbB-2 phosphorylation on tyrosine residues, is inhibited by treatment with a combination of mAb. T47D cells were incubated for 12 h with either L26, Herceptin™ (Her), a mixture of both (mix) or polyclonal antibodies (pAb) (total: 10 μg/ml). Cells were then washed and stimulated with NDF (50 ng/ml) for 15 min, lysed and immunoblotted with antiphosphotyrosin Abs, anti p-Erk Ab, and anti Erk2 Abs. FIG. 5b is a bar graph showing that NDF stimulation of transcription from the serum response element (as shown by the activity of a c-fos promoter-luciferase reporter gene) is inhibited by treatment with a combination of mAb. MCF-7 cells were transfected with a reporter plasmid, and, 24 h later, cells were split and incubated for 12 h with the indicated Abs, including a control human IgG. Later (47 h), cells were washed and stimulated for 1 h with NDF (50 ng/ml), followed by analysis using a luminator. FIG. 5c is a photograph showing that differentiation of tumor cells is higher in cells treated with a combination of mAb. AU-565 cells were treated for 3 d with mAbs (30 μg/ml) and then stained for neutral lipids (which are the product of differentiated tumor cells). FIG. 5d is a bar graph showing tumor volume of tumors from CD-1/nude mice that were injected s.c. with 3×10$^6$ N87 cells. mAbs (600 μg per animal) were injected i.p. 3, 7, and 10 d later. Saline-injected mice were used for control. Tumor volumes were measured after 18 d, and the mean volume of each group of four mice was plotted. The difference between treatments with each mAb alone and their combination is statistically significant (P<0.05). FIG. 5e is a diagram which shows the size of ErbB-Ab complexes formed at the cell surface is larger when the lattice is formed by more than one mAb. According to the model, the rate of internalization is proportional to the size of surface-associated antigen-Ab lattices; and FIGS. 6a-b is a schematic presentation of teravalent bi-epitopic antibodies to ErbB-2. The design of each bi-epitopic arm of the antibody is shown in FIG. 6a, along with the sequence of linkers. FIG. 6b shows an assembled disulfide-held tetravalent antibody.

DESCRIPTION OF THE PREFERRED EMBODIMENTS

The present invention relates to methods of identifying combinations of antibodies with a combined improved anti tumor activity. The present invention further relates to pharmaceutical compositions comprising such antibodies and methods of using same. Specifically, the present invention can be used for the treatment of receptor-tyrosine kinases associated diseases, such as cancer.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Overexpression and aberrant function of receptor tyrosine kinases (RTKs) and their ligands have been reported in many human cancers, providing a rationale for targeting this signaling network with novel approaches. The ErbB family of receptor tyrosine kinases is a selective target for inhibiting cancers because their activation often confers a proliferative advantage. For example, activation of the ErbB-1 tyrosine kinase provides signals that drive deregulated proliferation, invasion, metastasis, angiogenesis, and cell survival, and its inhibition has potential in both the treatment and prevention of these malignancies. Based on the structure and function of RTKs, therapeutic strategies have been developed. These include the use of human monoclonal antibodies (mAbs) generated against the receptor's ligand-binding extracellular domain. These mAbs block binding of receptor-activating ligands, and, in some cases, can induce receptor endocytosis and downregulation. Early clinical studies suggest only limited therapeutic activity in many common malignancies.

In order to improve the efficacy of antibody therapy, the use of mAb combinations had been attempted. Indeed a number of studies have been effected using at least two antibody combinations directed at distinct epitopes of ErbB-2 However, while some were successful in improving tumor inhibition, others reported only marginal or additive effect of such combinations when compared to a single antibody treatment.

These results suggest that selection of antibody combination only upon structural characteristics (i.e., binding to distinct epitopes) cannot be used as a sole criterion for selecting winning antibody combinations for therapy.

While reducing the present invention to practice, the present inventors uncovered that a combination of at least two antibodies to a receptor tyrosine kinase (RTK) of interest, which is selected capable of inducing synergistic endocytosis of the RTK, mediate improved antitumorigenic activity when compared to the effect of each individual antibody.

As is illustrated in the Examples section which follows, the present inventors showed that combinations of anti-EGFR or ErbB-2 mAbs directed at distinct extracellular epitopes better down-regulate the receptor than treatment with each monoclonal antibody alone (see Examples 1 and 3 of the Examples section which follows). The present inventors further showed that antibody combinations with improved therapeutic efficacy are those which are capable of synergistic down-regulation of the cell-surface receptor (see Examples 5 of the Examples section which follows). Thus, for example, co-administration of L26 and Herceptin™ resulted in augmented reduction of tumor volume as compared to the effect of each antibody alone. Accordingly, it is expected that co-administration of 565+111 will exhibit a better therapeutic effect than of 143+565 although both combinations are directed at distinct epitopes of the EGFR. The hybridoma cell lines expressing antibodies 111 and 565 were deposited pursuant to the Budapest Treaty requirements at the Collection Nationale de Cultures de Microorganismes (CNCM) Institut Pasteur 25, Rue du Docteur Roux F-75724 Paris CEDEX 15, on Nov. 26, 2009 and are registered as CNCM I-4261 for anti-EGFR antibody 111 and CNCM I-4262 for anti-EGFR antibody 565.

FIG. 5e outlines the proposed model. Accordingly, because of their bivalence, mAbs are able to form receptor homodimers, but treatment with combinations of mAbs will generate much larger receptor-Ab complexes. For several reasons it is proposed that the rate of endocytosis of mAb-RTK complexes is proportional to their size, in analogy to the entry of viruses and other polyvalent ligands and pathogens. Firstly, both mAb combinations and a pAb (FIG. 3b) induce earlier (FIG. 2b) and more extensive receptor internalization. Secondly, the observed bell-shaped dose-response (FIG. 2d), as well as the ability of a secondary Ab to increase receptor degradation (FIG. 2d), may be interpreted in terms of a precipitin reaction occurring at the cell surface. Thirdly, the strict dependence of mAb cooperation on simultaneous engagement of more than one epitope (FIGS. 2c and 3a), in line with previous reports (Damke, H., et al., J. Cell Biol. 127:915-934, 1994), is compatible with the notion that large surface aggregates internalize faster than smaller complexes.

Based on the overall structural similarity and endocytic mechanism of RTKs it is suggested that the present findings can be extended to the targeting of any RTK.

Thus, the present invention offers strategies to enhance the therapeutic efficacy of clinically approved antibodies such as Avastin™, Herceptin™ and C225/Cetuximab™.

Thus, according to one aspect of the present invention there is provided a method of identifying a combination of antibodies with a combined improved anti tumor activity.

As used herein the phrase "anti tumor activity" refers to prevention of tumor formation and/or reduction of tumor size (e.g., volume) and/or metastasis potential.

The method comprising identifying at least two anti RTK antibodies capable of inducing synergistic endocytosis of said RTK in a cell expressing said RTK, thereby identifying the combination of antibodies with the combined improved anti-tumor activity.

As used herein the term "RTK" refers to the cell surface form of protein tyrosine kinase (E.C. 2.7.1.112) which cellular surface expression/activation is typically associated with the onset or progression of a disease, usually a malignant disease, such as cancer.

Examples of RTKs which can be used in accordance with this aspect of the present invention are listed in Table 1 below.

TABLE 1

| Full name | Reference | Accession number | Examples of associated Pathologies | RTK | RTK subfamily |
|---|---|---|---|---|---|
| epidermal growth factor receptor | Silvestri GA and Rivera MP, Chest. 128(6): 3975-84, 2005. Snyder LC, et al., Clin Colorectal | NP_958441 | non-small cell lung cancer colorectal cancer head and neck cancer | EGFR/ErbB-1/HER1 | ErbB subfamily |

TABLE 1-continued

| Full name | Reference | Accession number | Examples of associated Pathologies | RTK | RTK subfamily |
|---|---|---|---|---|---|
| | Cancer. 12: S71-80, 2005. | | | | |
| | Slamon DJ, et al,. Science 244: 707-712, 1989. | Sprot: P04626 | breast ovarian and lung cancer | ErbB-2/HER2 | ErbB subfamily |
| | Visakorpi T, et al., Clin. Cancer Res. 9 (14), 5346-5357 (2003) | | transitional cell carcinoma of the bladder | | |
| | Huynh H, et al., Int. J. Oncol. 23 (3), 821-829 (2003) | | prostate cancer | | |
| Tyrosine kinase-type cell surface receptor HER3 | van der Horst EH, et al., Int. J. Cancer 115 (4): 519-527, 2005 | NP_001005915 | breast cancer | ErbB-3/HER3 | ErbB subfamily |
| | Visakorpi T, et al., Clin. Cancer Res. 9 (14): 5346-5357, 2003 | | transitional cell carcinoma of the bladder | | |
| | Huynh, H., et al., Int. J. Oncol. 23 (3), 821-829 (2003) | | prostate cancer | | |
| | Kobayashi, M., et al., Oncogene 22 (9), 1294-1301 (2003) | | adenocarcinoma | | |
| | de Vicente et al., Med Oral. 8(5): 374-81, 2003 | | oral squamous cell carcinoma | | |
| | de Vicente et al., Med Oral. 8(5): 374-81, 2003 | Q15303 | oral squamous cell carcinoma | ErbB-4/HER4 | ErbB subfamily |
| | Merimsky O., et al., Oncol Rep. 10(5): 1593-9, 2003 | | bone sarcoma | | |
| platelet-derived growth factor receptor alpha | Matsuda, M., et al, J. Neural Transm. 17 (1), 25-31, 1997 | Sprot: P16234 | glomerulonephritis (non cancer) | PDGFR alpha | platelet-derived growth factor receptor subfamily |
| | Wilczynski, SP. et al., Hum. Pathol. 36 (3), 242-249, 2005 | | epithelial ovarian cancers | | |
| | Ebert, M., et al., Int. J. Cancer 62 (5), 529-535, 1995 | | human pancreatic cancer | | |
| platelet-derived growth factor receptor beta | Tamborini E, et al., Clin. Cancer Res. 10 (3): 938-943, 2004 | NP_002600 (precursor) | synovial sarcoma | PDGFR beta | platelet-derived growth factor receptor subfamily |
| | Matsuda M, et al., J. Neural Transm. 17 (1): 25-31, 1997 | | glomerulonephritis (non cancer) | | |
| | Wilczynski SP,. et al., Hum. Pathol. 36 (3): 242-249, 2005 | | epithelial ovarian cancers | | |
| | Ebert M, et al., Int. J. Cancer 62 (5): 529-535, 1995 | | pancreatic cancer | | |
| vascular endothelial growth factor | Longatto FA, et al., Pathol Res Pract.; 201(2): 93-9, 2005 | NP_891555 | breast cancer | Flt-4/VEGFR-3 | platelet-derived growth factor |

TABLE 1-continued

| Full name | Reference | Accession number | Examples of associated Pathologies | RTK | RTK subfamily |
|---|---|---|---|---|---|
| receptor | Kojima H, et al., Cancer 104 (8): 1668-1677, 2005 | | lung adenocarcinoma | | receptor subfamily |
| fms-related tyrosine kinase 3/Vascular endothelial growth factor receptor 3 | Schmidt-Arras D, et al., Curr Pharm. 10(16): 1867-83, 2004 Van Vlierberghe P., et al., Blood 106 (13): 4414-4415, 2005 | NP_004110 | hematologic malignancies: acute myeloid leukemia pediatric T-cell acute lymphoblastic leukemias | Flt-3 | platelet-derived growth factor receptor subfamily |
| hepatocyte growth factor receptor | Dietrich S, et al., J. Environ. Pathol. Toxicol. Oncol. 24(3): 149-62, 2005. | NP_000236 (Precursor) | upper aerodigestive malignancies | c-MET/HGFR | hepatocyte growth factor receptor subfamily |
| ephrin receptor EphA2 | Ireton RC and Chen J,: Curr. Cancer Drug Targets. (3): 149-57, 2005 | NP_004422 (Precursor) | breast, prostate, lung, and colon cancers | EphA2/Eck | ephrin receptor family |
| ephrin receptor EphB4 | Xia G, et al., Cancer Res. 65 (11): 4623-4632, 2005 | NP_004435 (Precursor) | prostate cancer | EphB4 | ephrin receptor family |
| | Malavaud, B., Oncogene 23 (40): 6769-6778, 2004 Kranenburg, A. et al., R. Am. J. Respir. Cell Mol. Biol. 27 (5): 517-525, 2002 | NP_056934 (precursor) | stem cell leukemia lymphoma syndrome (SCLL) bladder carcinoma chronic obstructive pulmonary disease (non cancer) | FGFR1 | fibroblast growth factor receptor family |
| keratinocyte growth factor receptor | de Ravel TJ, et al., Eur. J. Hum. Genet. 13 (4), 503-505, 2005 Jang JH, et al., Cancer Res. 61 (9), 3541-3543 (2001) Kurban G, et al., Oncol. Rep. 11 (5): 987-991, 2004 | NP_075265 precursor) | Crouzon syndrome (non cancer) gastric and colorectal cancers uterine cervical cancer | KGFR/FGFR2 | fibroblast growth factor receptor family |
| fibroblast growth factor receptor 3 | L'Hote CG, and Knowles MA Exp. Cell Res. 304(2): 417-31, 2005 | NP_075254 (precursor) | multiple myeloma, cervical carcinoma and carcinoma of the bladder | FGFR3 | fibroblast growth factor receptor family |
| Epithelial discoidin domain receptor 1 | Matsuyama W, et al., Am. J. Respir. Cell Mol. Biol. 33 (6): 565-573, 2005 Heinzelmann-Schwarz VA, et al., Clin. Cancer Res. 10 (13): 4427-4436, 2004 | NP_054699 | pulmonary sarcoidosis (non cancer) breast, ovarian, esophageal, and pediatric brain tumors | DDR1 | Insulin receptor subfamily |
| insulin-like growth factor 1 receptor | Knowlden JM, et al., Endocrinology 146 (11): 4609-4618, 2005 | NP_000866 (precursor) | breast cancer | IGF1R | Insulin receptor subfamily |

TABLE 1-continued

| Full name | Reference | Accession number | Examples of associated Pathologies | RTK | RTK subfamily |
|---|---|---|---|---|---|
| Proto-oncogene tyrosine-protein kinase MER | Gal, A., Nat. Genet. 26 (3), 270-271 (2000) | Q12866 (precursor) | retinitis pigmentosa (non cancer) | MERTK | Axl/Ufo subfamily |
| AXL receptor tyrosine kinase | Chung BI, et al., DNA Cell Biol. 22 (8): 533-540, 2003 | NP_001690 | renal cell carcinoma | Axl/Ufo | Axl/Ufo subfamily |
| | Ito M, Thyroid 12 (11), 971-975, 2002 | | pediatric thyroid carcinomas | | |
| | Sun WS, et al., Mol. Hum. Reprod. 8 (6): 552-558 2002 | | ovarian endometriosis (non cancer) | | |
| | O'Bryan J. P., Mol. Cell. Biol. 11: 5016-5031 (1991). | | human myeloid leukemia | | |

Antibodies of this aspect of the present invention can be selected from pre-existing antibodies (e.g., publicly available hybridomas or recombinant antibody libraries, further described hereinbelow) or from newly generated antibodies produced according to methods which are well-known in the art and further described hereinbelow.

As mentioned, the combination of antibodies of this aspect of the present invention is identified as capable of inducing synergistic endocytosis of the RTK in a cell (e.g., mammalian cell) expressing same.

As used herein the term "endocytosis" refers to the removal of specific proteins (e.g., RTK) from the cell surface. Endocytosis of the present invention preferably results with receptor degradation which may be ubiquitin (as well as c-Cbl) dependent or independent (as described in Example 1 of the Examples section which follows).

As used herein the phrase "synergistic endocytosis" refers to the ability of the combined antibodies to remove the target RTK from the cell-surface in a total effect that is greater than the sum of the individual effects of each individual antibody.

Assaying endocytosis of the antibodies of the present invention can be effected using numerous biochemical and cell biology methods (e.g., microscopy) which are well known in the art. Examples of such methods are described at length in the Examples section which follows.

According to one preferred embodiment of this aspect of the present invention, the antibodies are directed at distinct extracellular epitopes of the RTK of interest. Methods of assaying epitope specificity of antibodies are well known in the art, such as for example, assaying antibody cross-competition as described at length in Example 2 of the Examples section which follows.

Antibodies of this aspect of the present invention may bind the RTK with similar or different affinities. According to another preferred embodiment of this aspect of the present invention, the antibodies bind the target RTK with a minimal affinity of at least 1 μM, 200 nM, 100 nM, 1 nM or higher.

Without being bound by theory it is suggested that synergistic endocytosis of the combination of antibodies of the present invention is dependent on the size of antibody-receptor lattices formed at the cell-surface, which dictates the rate of endocytic clearance and extent of signaling blockade.

Thus, antibodies of the present invention are preferably at least bivalent (e.g., of the IgG subtype) or more (e.g., of the IgM subtype). It will be appreciated that monovalent antibodies may be used however measures should be taken to assemble these to larger complexes such as by using secondary antibodies (or using other cross-linkers which are well known in the art).

As used herein the term "antibodies" refers to antibodies and antibody fragments.

As used herein the term "antibody" refers to a substantially intact antibody molecule.

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Cloning immunoglobulin variable domains for expression by the polymerase chain reaction. Proc Natl Acad Sci USA 86, 3833-3837; and Winter, G. and Milstein, C. (1991). Man-made antibodies. Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Continuous cultures of fused cells secreting antibody of predefined specificity. Nature 256, 495-497; Kozbor, D. et al. (1985). Specific immunoglobulin production and enhanced tumorigenicity following ascites growth of human hybridomas. J Immunol Methods 81, 31-42; Cote R J. et al. (1983). Generation of human monoclonal antibodies reactive with cellular antigens. Proc Natl Acad Sci USA 80, 2026-2030; and Cole, S. P. et al. (1984). Human monoclonal antibodies. Mol Cell Biol 62, 109-120).

In cases where target antigens are too small to elicit an adequate immunogenic response when generating antibodies in vivo, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill., USA. The resulting immunogenic complex can then be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove.

Antibody fragments may be obtained using methods well known in the art. (See, for example, Harlow, E. and Lane, D. (1988). Antibodies: A Laboratory Manual, Cold Spring Harbor Laboratory, New York.) For example, antibody fragments according to the present invention can be prepared by proteolytic hydrolysis of the antibody or by expression in E. coli or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, an (Fab')2 antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647; and Porter, R. R. (1959). The hydrolysis of rabbit γ-globulin and antibodies with crystalline papain. Biochem J 73, 119-126). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

As described hereinabove, an Fv is composed of paired heavy chain variable and light chain variable domains. This association may be noncovalent (see, for example, Inbar, D. et al. (1972). Localization of antibody-combining sites within the variable portions of heavy and light chains. Proc Natl Acad Sci USA 69, 2659-2662). Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single-chain Fvs is provided in the literature of the art (see, e.g.: Whitlow, M. and Filpula, D. (1991). Single-chain Fv proteins and their fusion proteins. METHODS: A Companion to Methods in Enzymology 2(2), 97-105; Bird, R. E. et al. (1988). Single-chain antigen-binding proteins. Science 242, 423-426; Pack, P. et al. (1993). Improved bivalent miniantibodies, with identical avidity as whole antibodies, produced by high cell density fermentation of Escherichia coli. Biotechnology (N.Y.) 11(11), 1271-1277; and U.S. Pat. No. 4,946,778).

Isolated complementarity-determining region peptides can be obtained by constructing genes encoding the CDR of an antibody of interest. Such genes may be prepared, for example, by RT-PCR of the mRNA of an antibody-producing cell. Ample guidance for practicing such methods is provided in the literature of the art (e.g., Larrick, J. W. and Fry, K. E. (1991). PCR Amplification of Antibody Genes. METHODS: A Companion to Methods in Enzymology 2(2), 106-110).

The present invention also envisages bispecific antibodies. In this case, antibodies or antibody fragments may be fused using standard recombinant technology so as to generate bispecific antibodies having dual specificity (e.g., 565 and 111 for targeting EGFR). For guidance regarding suitable production and use of bispecific antibodies, refer for example, to: Kipriyanov S M, Le Gall F. et al., 2004. Recent advances in the generation of bispecific antibodies for tumor immunotherapy. Curr Opin Drug Discov Devel. 7:233-42; Peipp M, Valerius T., 2002. Bispecific antibodies targeting cancer cells. Biochem Soc Trans. 30:507-11; and Kriangkum J. et al., 2001. Bispecific and bifunctional single chain recombinant antibodies. Biomol Eng. 18:31-40 (see Example 6 of the Examples section).

It will be appreciated that for human therapy or diagnostics, humanized antibodies are preferably used. Humanized forms of non-human (e.g., murine) antibodies are genetically engineered chimeric antibodies or antibody fragments having (preferably minimal) portions derived from non-human antibodies. Humanized antibodies include antibodies in which the CDRs of a human antibody (recipient antibody) are replaced by residues from a CDR of a non-human species (donor antibody), such as mouse, rat, or rabbit, having the desired functionality. In some instances, the Fv framework residues of the human antibody are replaced by corresponding non-human residues. Humanized antibodies may also comprise residues found neither in the recipient antibody nor in the imported CDR or framework sequences. In general, the humanized antibody will comprise substantially all of at least one, and typically two, variable domains, in which all or substantially all of the CDRs correspond to those of a non-human antibody and all or substantially all of the framework regions correspond to those of a relevant human consensus sequence. Humanized antibodies optimally also include at least a portion of an antibody constant region, such as an Fc region, typically derived from a human antibody (see, for example: Jones, P. T. et al. (1986). Replacing the complementarity-determining regions in a human antibody with those from a mouse. Nature 321, 522-525; Riechmann, L. et al. (1988). Reshaping human antibodies for therapy. Nature 332, 323-327; Presta, L. G. (1992b). Curr Opin Struct Biol 2, 593-596; and Presta, L. G. (1992a). Antibody engineering. Curr Opin Biotechnol 3(4), 394-398).

Methods for humanizing non-human antibodies are well known in the art. Generally, a humanized antibody has one or more amino acid residues introduced into it from a source which is non-human. These non-human amino acid residues are often referred to as imported residues, which are typically taken from an imported variable domain. Humanization can be performed essentially as described (see, for example: Jones et al. (1986); Riechmann et al. (1988); Verhoeyen, M. et al. (1988). Reshaping human antibodies: grafting an antilysozyme activity. Science 239, 1534-1536; and U.S. Pat. No. 4,816,567), by substituting human CDRs with corresponding rodent CDRs. Accordingly, humanized antibodies are chimeric antibodies, wherein substantially less than an intact human variable domain has been substituted by the corresponding sequence from a non-human species. In practice, humanized antibodies may be typically human antibodies in which some CDR residues and possibly some framework residues are substituted by residues from analogous sites in rodent antibodies.

Human antibodies can also be produced using various additional techniques known in the art, including phage-display libraries (Hoogenboom, H. R. and Winter, G. (1991). By-passing immunization. Human antibodies from synthetic repertoires of germline VH gene segments rearranged in vitro. J Mol Biol 227, 381-388; Marks, J. D. et al. (1991). By-passing immunization. Human antibodies from V-gene libraries displayed on phage. J Mol Biol 222, 581-597; Cole et al. (1985), Monoclonal Antibodies and Cancer Therapy, Alan R. Liss, Inc., pp. 77-96; and Boerner, P. et al. (1991). Production of antigen-specific human monoclonal antibodies from in vitro-primed human splenocytes. J Immunol 147, 86-95). Humanized antibodies can also be created by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807; 5,545,806; 5,569,825; 5,625,126; 5,633,425; and 5,661,016; Marks, J. D. et al. (1992). By-passing immunization: building high affinity human antibodies by chain shuffling. Biotechnology (N.Y.) 10(7), 779-783; Lonberg et al., 1994. Nature 368:856-859; Morrison, S. L. (1994). News and View: Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human mAbs in mice. Nat Biotechnol 14, 826; and Lonberg, N. and Huszar, D. (1995). Human antibodies from transgenic mice. Int Rev Immunol 13, 65-93).

After antibodies have been obtained, they may be tested for activity, for example via enzyme-linked immunosorbent assay (ELISA).

Antibodies identified using the teachings of the present invention are adventitiously used in therapy of RTK-associated diseases or disorders.

As used herein the phrase "RTK-associated disease or disorder" refers to a disease or disorder which is dependent on RTK activity or expression for onset or progression. Typically such are cellular proliferation disorders e.g., cancer. The above Table 1 lists exemplary RTK and their associated pathologies.

Thus, according to another aspect of the present invention there is provided a method of treating cancer in a subject. The method comprising administering to a subject in need thereof a therapeutically effective amount of the subject.

As used herein the term "subject" refers to a mammal, preferably a human subject.

As used herein the term "treating" refers to alleviating or diminishing a symptom associated with a disease (e.g., cancerous disease). Preferably, treating cures, e.g., substantially eliminates, the symptoms associated with the disease.

Antibodies of the present invention can be administered to an organism per se, or in a pharmaceutical composition where they are mixed with suitable carriers or excipients (either individually or in a co-formulation).

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the antibodies accountable for the intended biological effect.

Hereinafter, the phrases "physiologically acceptable carries" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

It will be appreciated that the antibodies of the present invention can be provided to the individual with additional active agents to achieve an improved therapeutic effect as compared to treatment with each agent by itself. In such therapy, measures (e.g., dosing and selection of the complementary agent) are taken to adverse side effects which may be associated with combination therapies.

Administration of such combination therapy can be simultaneous, such as in a single capsule having a fixed ration of these active agents, or in multiple capsules for each agent.

Thus, for example, the antibodies of the present invention can be administered along with analgesics, chemotherapeutic agents, radiotherapeutic agents and other treatment regimens which are well known in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Anti-EGFR Abs Mediate Distinct Endocytic Pathway of EGFR as Compared to Ligand Mediated Receptor Endocytosis To compare EGF- and mAb-induced receptor down-regulation, a series of mAbs were generated and three mAbs were analyzed for their ability to displace cell surface-bound EGF molecules. Ab-induced down-regulation of EGFR was evaluated in KB cells treated with EGF or mAbs. Ubiquitylation was tested in CHO cells ectopically expressing EGFR, c-Cbl, and hemagglutinin-ubiquitin, and treated with either EGF or mAb.

Materials and Methods

Materials—Unless otherwise indicated, materials were purchased from Sigma (St. Lewis, USA). Abs were purchased from Santa Cruz Biotechnology (Santa Cruz, Calif., USA), except for anti-hemagglutinin (Roche, Basel, Switzerland).

Generation of anti-EGFR antibodies—To generate mAbs to EGFR, mice were immunized with an IgB-1, a fusion protein consisting of the extracellular domain of EGFR fused to the Fc region of human IgG {IgB1 described by X. Chen et al. [JBC 271, 7620-7629 (1996) An immunological approach reveals biological differences between the two NDF/heregulin receptors, ErbB-3 and ErbB-4}. Hybridomas were screened for inhibition of binding of a radiolabeled EGF to the surface of A-431 cells (ATCC Accession No. CRL1555). The Ig fraction was purified by using a column of protein A.

Receptor Down-Regulation and mAb-Binding Assays—KB cells (ATCC Accession No. CCL-17) were incubated at 37° C. for different time periods in binding buffer containing EGF (100 ng/ml) or mAb (20 μg/ml). The cells were then washed at 4° C. and acid-stripped (0.15 M acetic acid/0.15 M NaCl; 4 min) to remove surface-bound ligands. The number of surface binding sites was determined by incubating the cells at 4° C. with [$^{125}$I]EGF (5 ng/ml) for 1.5 h.

Surface Biotinylation, and Immunoblotting—KB cells were incubated at 37° C. for 4 h or 32 h in a binding buffer containing EGF (100 ng/ml) or mAb (20 μg/ml). The cells were then washed and acid-stripped (0.15 M acetic acid/0.15 M NaCl; 4 min) to remove surface-bound ligands. Thereafter, cells were washed and incubated for 60 min at 4° C. with N-hydroxysuccinimide-biotin (0.5 mg/ml; Calbiochem, Merck KGaA, Darmstadt, Germany). Coupling of biotin was blocked with 15 mM glycine. This was followed by immunoprecipitation and blotting with streptavidin-horseradish peroxidase. In the absence of immunoprecipitation cells were immunoblotted with an anti-EGFR antibody. The compositions of buffers, as well as the protocols for immunoprecipitation and immunoblotting were as described (Klapper, L. N., et al., Oncogene 14: 2099-2109, 1997).

Transfections—Transfections (1-2 μg of DNA per 90-mm plate) were performed by using the calcium phosphate or the Lipofectamine methods.

Plasmid Construction—The construction of Wild-Type (WT) and Y1045F-EGFR vectors has been described (Waterman, H., et al., EMBO J. 21: 303-313, 2002).

Ubiquitylation detection assays—CHO cells (ATCC Accession No. —CCL-51) transiently expressing EGFR, c-Cbl, and hemagglutinin-ubiquitin were incubated with EGF (100 ng/ml; 1 h), saline, or the indicated mAbs (10 μg/ml; 18 h). EGFR was analyzed by immunoprecipitation and immunoblotting after removal of bound ligands.

Recruitment of c-Cbl—CHO cells transiently expressing WT- or Y1045F-EGFR, along with c-Cbl, were incubated with EGF (100 ng/ml; 1 h), saline, or the indicated mAbs (10 μg/ml; 18 h). EGFR was analyzed by immunoprecipitation and immunoblotting after removal of bound ligands.

Results

Anti-EGFR Abs induce slow, ubiquitylation-independent receptor down-regulation—To compare EGF- and mAb-induced receptor down-regulation, a series of three mAbs, which were selected for their ability to displace cell-surface bound EGF molecules. Ab-induced down-regulation of EGFR was evaluated in KB cells treated with EGF or mAbs. Whereas internalization induced by EGF removed most (80%) receptors within 10 min, the three mAbs induced significantly slower endocytosis (FIG. 1a). To directly assess EGFR internalization, cells were surface-labeled with biotin after incubation with mAbs or EGF (FIG. 1b).

In conclusion: mAb-induced internalization and degradation of EGFR is slow relative to EGF-induced receptor internalization (FIG. 1b).

The robustness of EGF-induced down-regulation is attributed to c-Cbl mediated conjugation of ubiquitin to EGFR. To test ubiquitylation, CHO cells ectopically expressing EGFR, c-Cbl, and hemagglutinin-ubiquitin were used. Unlike EGF-treated cells, cells treated with mAb displayed faint, if any ubiquitylation of EGFR (FIG. 1c). When using a mutant form of EGFR, Y1045F, which cannot directly recruit c-Cbl (Waterman, H., et al., EMBO J. 21: 303-313, 2002], a nearly normal down-regulation of the mutant was evident in response to treatment with mAbs (FIG. 1d). The same mutant exhibited resistance to EGF-induced degradation (FIG. 1d). In conclusion, unlike the ligand-induced process, Cbl-mediated ubiquitylation may not be involved in antibody induced internalization.

Example 2

Combinations of Anti-Receptor mAbs Directed at Distinct Epitopes Better Down-Regulate EGFR than each mAb Alone The ability of antibody combinations to down-regulate EGFR was assessed.

Materials and Methods

Materials—As described in Example 1.

Generation of anti-EGFR antibodies—Generation of antibodies was done as described in Example 1.

Receptor Down-Regulation and mAb-Binding Assays—KB cells were incubated at 37° C. for 13 hours in binding buffer containing EGF (100 ng/ml) or mAb in different combinations (total: 20 μg/ml) EGFR was analyzed by immunoblotting after removal of bound ligands.

Cross competition analysis—KB cells were treated for 1 h at 4° C. with mAbs 111, 143, 565, or EGF (10 ng/ml). Radio-labeled mAbs (8 nM) were then added, and the cells were incubated for an additional 15 min before determination of radioactivity.

Immunuoblotting—The compositions of buffers, as well as the protocols for immunoprecipitation and immunoblotting were as described (Klapper, L. N., et al., Oncogene 14: 2099-2109, 1997).

Analysis of Lattice size of mAb, a second antibody and receptor, and its effect on receptor degradation—KB cells were preincubated with saline, EGF (100 ng/ml), or a constant amount of either one of the two, or both 565 and 111 mAb (total: 10 μg/ml) for 3 h at 4° C. The medium of all cells (except cells treated with both mAb) was then replaced with fresh medium containing increasing amounts of goat anti-mouse IgG [second Ab: either 40 (+) or 10, 20, and 40 μg/ml]. Cells were then incubated for an additional 18 h at 37° C., and were analyzed for EGFR by immunoblotting after removal of bound ligands.

Results

The effect of mAb combinations on receptor down regulation—In an attempt to increase efficacy of down-regulation, mAb combinations were tested (FIG. 2a). Although each mAb alone induced limited down-regulation after a 13 h incubation, two mAb combinations dramatically increased receptor degradation. Down-regulation of EGFR by the more effective combination was not only more extensive than each Ab alone, but also evolved more rapidly (FIG. 2b).

The effect of epitope distinction in mAb pairs, on receptor down regulation—To understand why certain combinations are more effective, cross-competition analyses was formed using radiolabeled mAbs (FIG. 2c). The results confirmed that each mAb is displaceable by an unlabeled EGF and showed that the nonsynergistic mAbs are cross-competitive, whereas Abs of the synergistic combinations bind distinct epitopes.

The effect of antigen-Ab lattice on receptor internalization—Because mAbs that share binding sites form EGFR dimers, whereas combinations of Abs recognizing distinct epitopes will form larger lattices it was assumed that the rate of EGFR removal from the cell surface is proportional to the size of antigen-Ab lattices. Two predictions raised by this model were experimentally tested. First, lattices are expected to dissociate at very high Ab concentrations because of monovalent binding to EGFR. Indeed, when the concentration of mAb 565 was gradually increased, the extent of EGFR degradation after co-incubation with mAb 111 displayed a bell-shaped pattern (FIG. 2d). Secondly, when surface-bound mAbs were aggregated with a secondary anti-mouse IgG, an increase in EGFR degradation was observed (FIG. 2d Lower). As expected, the efficacy of down-regulation was reduced at high concentrations of the secondary Ab. The results support the possibility that antireceptor Abs drive internalization and subsequent degradation of EGFR in a mechanism that involves formation at the cell surface of Ab-receptor complexes analogous to the well characterized precipitin reaction occurring in solution.

Example 3

Combinations of Anti-Receptor mAbs Directed at Distinct Epitopes Better Down-Regulate ErbB-2 than Each mAb Alone To extend the above observations to another RTK, ErbB-2, a combination of two Abs that recognize distinct epitopes on ErbB-2 were selected. Levels of surface receptors and internalized receptors, were compared as a response to treatment with separate and combination mAb, as well as polyclonal antibodies against ErbB-2.

Materials and Methods

Materials—Trastuzumab/Herceptin T was provided by Genentech (South San Francisco, Calif., USA). L26 was purchased from Santa Cruz Biotechnology (Santa Cruz, Calif., USA). 4D5 was previously described [Lewis G D, Figari I, Fendly B, et al. Differential responses of human tumor cell lines to anti-p185HER2 monoclonal antibodies. Cancer Immunol Immunother 37:255-263, (1993)].

Generation of anti-Erb-2 antibodies—To generate a polyclonal Ab (pAb) to ErbB-2, mice were immunized with an IgB-2, a fusion protein containing the extracellular domain of ErbB-2 fused to the Fc region of human IgG (detailed description is provided in X. Chen (1996) J. Biol. Chem. 271(13): 7620-9. The Ig fraction was purified by using a protein A column.

Cross competition analysis—The experiment was effected essentially as described above, only SKBR-3 Cells (ATCC Accession No. HTB-30) were treated at 4° C. for 1 hour with various concentrations of mAbs, L26 or Herceptin™. Radiolabeled mAbs L26 (8 nM) or Herceptin™ were then added, and the cells were incubated for 15 min. After washing, radioactivity was measured and expressed as average±SD.

Receptor Down-Regulation and mAb-Binding Assays—HEK-293T cells (J Elango, E M, et al., Appl Genet.; 45(4): 469-71, 2004) ectopically expressing ErbB-2 or T47D were treated with L26 and/or Herceptin™ (Her; total: 20 µg/ml), pAb or preimmune Ab at 37° C. for 0, 2, and 6 hours. Surface ErbB-2 was analyzed by immunoblotting after removal of bound ligands.

Analysis of Intracellular accumulation with fluorescein labeled Herceptin™—SKBR-3 cells (ATCC Accession No. HTB-30) were treated at 37° C. for a time period ranging from 0.5-4 hours with a fluorescein-labeled anti 4D5 (the parental form of Herceptin) mAb (10 µg/ml), in the absence or presence of L26-mAb. Thereafter, cells were washed and acid-stripped. Internalized 4D5 was determined by using a cell sorter, as described below.

Immunofluorescence and Flow Cytometry—Following the indicated treatment with mAbs, cells were fixed with paraformaldehyde (3%) and permeabilized in saline containing 1% albumin and 0.2% Triton X-100. Cells were then incubated for 30 min at 22° C. with a Cy3-conjugated donkey-anti-mouse F(ab)$_2$ Ab. The coverslips were mounted in mowiol and examined with a Zeiss Axiovert confocal microscope.

For flow cytometric analyses, cells were incubated for 1 h at 4° C. in a saline buffer containing 0.1% albumin and FITC-conjugated 4D5 Ab (10 µg/ml) and then transferred to 37° C. to allow internalization. Surface-bound mAbs were removed and cells resuspended and analyzed by flow cytometry to detect internalized mAbs. To determine background signals, cells were incubated with the mAb at 4° C. and acid-stripped without transferring to 37° C.

Results

Distinct epitope binding antibodies to ErbB-2—FIG. 3a shows that the two selected anti-ErbB-2 antibodies: L26, which inhibits heterodimerization of ErbB-2 and Herceptin, recognize distinct epitopes. A cell surface-bound L26 could not be displaced by a large molar excess of Herceptin, and L26 did not affect Herceptin™ binding (FIG. 3a).

The effect of mAb combination on the efficiency of ErbB-2 internalization—As expected, a 6-h treatment with a mixture of L26 and Herceptin™ resulted in a close to complete disappearance of ErbB-2, but neither mAb alone significantly down-regulated ErbB-2 at this time point (FIG. 3b).

The effect of pAb binding and mAb combinations on the efficiency of ErbB-2 internalization—To test the prediction that a polyvalent Ab would induce extensive down-regulation, rabbit pAb to ErbB-2 were raised and the effects on receptor turnover were tested. As predicted, the pAb extensively down-regulated ErbB-2 (FIG. 3b).

Two additional tests confirmed the ability of mAbs to enhance endocytosis. First, using a fluorescent 4D5 (the parental form of Herceptin™) and an unlabeled L26, a robust intracellular accumulation of the fluorescent mAb was detected when cells were co-incubated with the other Ab (FIG. 3c). Likewise, confocal microscopy that followed the fate of cell-bound L26 by using a secondary Ab revealed enhanced endocytosis of L26 when combined with Herceptin™ (FIG. 3d).

Example 4

Down-Regulation of ErbB-2 by a Combination of mAbs is Dynamin-Dependent, and Requires no Cytoplasmic Receptor's Portions To address the mechanism underlying endocytosis of ErbB-2, the dependence on dynamin (an endocytosis related protein) was tested using a dominant negative form of dynamin, and structural requirements of the receptor were tested using two mutant forms of the receptor, lacking the membrane spanning domain and/or the cytoplasmic domain.

Materials and Methods

Plasmid Transfections—Transfections were effected as described in Example 1 above.

Analysis of dynamin dependence—HEK-293T cells were cotransfected with plasmids encoding EGFR or ErbB-2, along with plasmids encoding c-Cbl (WT) and a dominant-negative form of dynamin (K44A). Following 48 h, cells were treated with EGF (100 ng/ml) or a combination of L26 and Herceptin™ (Her; total: 20 µg/ml), and extracts were analyzed for ErbB-2 or EGFR by immunoprecipitation and immunoblotting as described above.

Plasmid Construction—Two mutant forms of ErbB-2 were constructed. ECD-TM, that lacks the entire cytoplasmic domain, and ECD-GPI which is a lipid-anchored full extracellular domain of ErbB-2. The extracellular domain-transmembrane (ECD-TM) was constructed by introducing a stop codon at nucleotide 2176. To construct ECD-glycosyl-phosphatidylinositol (GPI), the GPI signal of the rat contactin-1 gene was fused to the 3' end of erbB-2 cDNA [at nucleotide 2106, similar construction described in Tzahar (1997) EMBO J. vol. 16, 4938-4950 Bivalence of EGF-like ligands drives the ErbB signaling network].

Results

Dynamin dependency of the endocytosis—To test the mechanism of Erb-2 endocytosis, the dependence on dynamin, a GTPase regulating the "pinching off" of endocytic vesicles at the plasma membrane was examined. It has previously been shown that a dominant-negative form of dynamin (K44A) blocks EGF endocytosis (Damke, H., et al., J. Cell Biol. 127:915-934, 1994). Hence, the effects of WT and K44A on EGF-induced down-regulation of EGFR were first confirmed. When ectopically expressed, along with EGFR and c-Cbl, K44A inhibited EGF-induced degradation of EGFR and enhanced receptor expression (FIG. 4a). When applied to ErbB-2, K44A almost abolished receptor down-regulation upon treatment of cells with a combination of mAbs (FIG. 4a Lower).

Structural requirements for mAb induced endocytosis—To address structural requirements for mAb induced endocytosis, two mutants, which are schematically presented in FIG. 4b were constructed. ECD-TM is an ErbB-2 molecule that lacks the entire cytoplasmic domain, whereas ECD-GPI is a lipid-anchored full extracellular domain of ErbB-2. When electrophoresed, both mutants displayed two bands corresponding to 120 and 135 kDa (FIG. 4c Lower). Surface biotinylation experiments revealed that only the 135-kDa species reached the plasma membrane, and analysis of sensitivity to endoglycosidase H indicated that maturation of the nascent 120-kDa species was defective (data not shown). In accordance, only the 135-kDa forms of ECD-TM and ECD-GPI underwent down-regulation upon treatment of cells with a mixture of mAbs (FIG. 4c). Taken together, these observations indicate that no cytoplasmic or transmembrane motifs of ErbB-2 are necessary for mAb-induced internalization and degradation.

Example 5

Combinations of Anti-ErbB-2 Abs Inhibit Growth Factor Signaling, Promote Differentiation, and Reduce Tumor Growth To test the effect of mAb combinations on ErbB2 signaling downstream factors of the erk pathway were examined following treatment with the antibodies. In addition, the exclusive effect of mAb combinations on tumor cell differentiation and growth was also analyzed Materials and Methods Analysis of the effect of pAb binding to ErbB-2 on Erb signaling—T47D mammary tumor cells (ATCC Accession No. HTB-133) were incubated for 12 h with mAbs (total: 10 µg/ml), including either individual, or a mixture of L26 and Herceptin, or anti ErbB-2 polyclonal antibodies. Cells were then washed and stimulated with NDF (50 ng/ml) for 15 min, and cell extracts were analyzed for phosphotyrosine as well as phosphorylated Erk and Erk-2 by immunoblotting.

Transcription analysis—MCF-7 Cells (ATCC Accession No. HTB-22) were transfected with a reporter pSRE-Fluc plasmid containing the serum response element cloned upstream to the c-fos promoter and the luciferase gene. Twenty-four hours later, cells were split and incubated for 12 h at 37° C. with various Abs, including a control human IgG, in medium containing 0.1% serum. Then cells were washed and stimulated 47 h later with Neu differentiation factor (NDF, 50 ng/ml) for 1 h at 37° C. Thereafter, cell extracts were prepared in a reporter lysis buffer (Promega, Madison Wis., USA), and after centrifugation (14,000 rpm for 15 min), 30-µl aliquots were incubated with 100 µl of luciferin buffer (0.1 M Tris-acetic acid/10 mM magnesium acetate/1 mM EDTA, pH 8.0/74 mM luciferin/2.2 mM ATP) and analyzed by using a luminator.

Antibody effect on neutral lipid formation—AU-565 (ATCC Accession No. CRL-2351) mammary tumor cells were treated for 3 d with mAbs (30 µg/ml) and then stained for neutral lipids. A modified "Oil Red O in propylene glycol" method was used to visualize neutral lipids (Bacus, S. S., et al., Cancer Res. 53: 5251-5261, 1993).

Analysis of the Effect of Combination mAb Binding on Tumor Retardation—

Female CD-1/nude mice were injected subcutaneously (s.c.) with $3 \times 10^6$ N87 human gastric cancer cells (ATCC Accession No. CRL-5822) overexpressing ErbB-2. mAbs (600 µg per animal) were injected intraperitoneally (i.p.) 3, 7, and 10 days later. Saline-injected mice were used for control. Groups of four mice were used. Tumor parameters were measured twice weekly, and the mean tumor volume of each group of four mice was plotted.

Results

Effect of mAb on down stream signaling of ErbB-2—Because ErbB-2 acts as a ligand-less coreceptor that augments growth factor signaling, Ab mixtures capable of down-regulation are expected to desensitize ErbB signaling. This model, was tested on the mitogen-activated protein kinase (Erk) pathway and the corresponding nuclear outcome, namely transcription from promoters containing the serum response element (Johansen, F. E. and Prywes, R. Mol. Cell. Biol. 14: 5920-5928, 1994). Treatment of T47D mammary tumor cells (ATCC Accession No. HTB-133) with NDF resulted in rapid stimulation of ErbB phosphorylation on tyrosine residues and activation of Erk (FIG. 5a). Significant signal reduction was observed in cells pretreated with mixtures of anti-ErbB-2 Abs, either a combination of two mAbs or a rabbit pAb.

Effect of mAb combinations on NDF stimulation of the serum response element—As shown in FIG. 5b, transcription from the serum response element was stimulated 8- to 12-fold by NDF, but pretreatment with Ab combinations, unlike Herceptin™ alone or a control Ig, almost completely blocked transcription (FIG. 5b).

Effect of mAb combination mammary tumor cell transformation—Treatment with mAbs to ErbB-2 transforms mammary tumor cells into well differentiated flat cells, which synthesize neutral lipids (Bacus, S. S., et al., Cancer Res. 53: 5251-5261, 1993). To examine possible Ab synergy on induction of mammary differentiation, cells were incubated with Herceptin, L26, or a combination and stained for neutral lipids 4 d later. The results demonstrate that each mAb is capable of inducing a differentiated phenotype, but a mixture of mAbs was significantly more effective (FIG. 5c), in line with more extensive down-regulation of ErbB-2.

Effect of mAb combination on tumor cell volume—Because previous studies related enhanced endocytosis of ErbB-2 to reduced tumorigenesis (Klapper, L. N., et al., Oncogene 14: 2099-2109, 1997; Hurwitz, E., et al., Proc. Natl. Acad. Sci. USA 92, 3353-3357, 1995], these cooperative effects raised the possibility that L26 and Herceptin™ will augment each other's ability to retard tumors. To test this prediction, mice were injected with N87 gastric cancer cells (ATCC Accession No. CRL-5822) overexpressing ErbB-2. Animals were injected with mAbs or their combination 3, 7, and 10 d later. FIG. 5d presents the results recorded at day 18. At this early time point, both L26 and Herceptin™ only partially inhibited tumor growth (30% and 17% inhibition, respectively), but their combination yielded a 70% reduction in tumor volume ($P<0.05$). In conclusion, a combination of anti-ErbB-2 mAbs that engage distinct epitopes synergistically inhibited the tumorigenic growth of ErbB-2-driven cancer cells, in line with enhanced ability of the mixture to down-regulate ErbB-2 and block growth factor signaling.

Example 6

Construction of Bi-Epitopic mAbs to ErbB-2

The present inventors have previously developed a series of mAbs to ErbB-2 and grouped them into sub-classes according to the antigenic determinants they recognize on ErbB-2 [Klapper et al., (1997) Oncogene 14, 2099-2109]. Because the two antigen-binding sites at the tips of the Fab arms are up to 150 Å apart and point in opposite directions [Harris et al., (1992) Nature 360, 369-372], a flexible structure is designed with several linkers while selecting specific pairs of non-competitive anti-ErbB-2 antibodies (see scheme in FIGS. 6a-b). The selection is based upon competition binding assays, in vitro experiments (receptor down-regulation; see above materials and methods), and effects of mAb mixtures on tumor growth in animals (see above Example 5).

Construction of bispecific antibodies—The design and cloning strategy of the bi-epitopic antibodies follows the principles used before to construct a tetravalent bi-specific antibody that binds to the Hepatitis B virus surface antigen [Park et al., (2000) Mol. Imm. 37, 1123-1130].

Essentially, chimeric antibodies are constructed by replacing the constant region of the murine mAbs with the constant region of human IgG1. In the next step, the cDNAs encoding the chimeric antibodiesis used to construct single-chain ScFv molecules. In each case, the C-terminus of the murine V-heavy domain is linked to the N-terminus of the murine V-light region through a 15 amino acid linker peptide (three tandem copies of Gly-Gly-Gly-Gly-Ser). In addition, the C-terminus of one antibody (e.g., L26) is linked to the N-terminus of the other antibody (e.g., our N12 antibody) via a 25 amino acid-long linker peptide (Park et al., 2000, above). The corresponding nucleotide sequence contains a SpeI site for cloning. The linked ScFvs are fused to the hinge region of human gamma-1 Fc region. The final construct contains two cysteine residues (Cys-226 and Cys-229) in order to retain inter-chain disulfide bonds. The recombinant gene is placed downstream of the human cytomegalovirus promoter in a dhfr gene amplification vector, which contains a neomycin resistant gene. Following expression in DHFR-deficient CHO cells, selection (in G418) and over-expression (under MTX), cell clones producing high quantities of two or more bi-epitopic antibodies are derived. The antibodies are purified using Protein A chromatography and their expected homodimeric structure, as well as dual specificity, and are tested by using gel electrophoresis and a competition binding assay that utilizes the radio-labeled parental mAbs.

Functional tests of bi-epitopic mAbs to ErbB-2—To evaluate the biological activities of recombinant bi-epitopic tetravalent antibodies, two reference molecules are used. The first one is a rabbit anti-ErbB-2 antiserum, which is extremely active in terms of receptor down-regulation and inhibition of cell growth. The other reference are the two parental mAbs. The 'surface lattice' model predicts that the bi-epitopic antibodies are more active than each mAb alone and comparable to the activity of the respective mixture of mAbs (or a polyclonal antibody). Nevertheless, due to steric effects, some bi-specific antibodies may not be able to simultaneously bind both target epitopes, which is expected to reduce their activity.

In vitro assays are thus performed with the set of bi-specific antibodies, mAbs and the polyclonal antiserum: Receptor down-regulation and degradation in living cells treated with antibodies, growth arrest of ErbB-2-expressing cells once treated with antibodies, and a mammary cell differentiation assay utilizing casein and lipid secretion, along with cell adhesion molecules, as markers of response [Bacus et al., (1992) Cancer Res 52, 2580-2589]. In addition, the recombinant antibodies are comparatively analyzed in cellular cytotoxicity assays, both antibody-dependent (ADCC) and complement-dependent (CDC), essentially as described [Flieger et al., (1995) J. Immunol. Methods 180, 1-13]. Ultimately, antigrowth activities of the bi-specific antibodies are examined in tumor-bearing animals using previously established model systems like T47D breast cancer cells, gastric cancer cells overexpressing ErbB-2 [Kasprzyk et al., (1992) Cancer Res 52, 2771-2776, and prostate cancer models, such as PC3.

In vivo experiments are performed only with bi-epitopic antibodies that are significantly more active in vitro than the respective parental mAbs. Male CB. 17-SCID mice are used as previously described in this application and elsewhere [Spiridon et al., (2002) Clin Cancer Res 8, 1720-1730]. Following cell inoculation and appearance of detectable tumors, mice are injected with the bi-epitopic antibodies, or the reference antibodies. Repeated injections are used in order to maintain high levels of the antibody in serum. Tumors are measured twice a week and the resulting growth curves are subjected to statistical analysis. In case the tetravalent bi-epitopic mAbs show significantly better abilities to retard tumor growth and extend survival of tumor-bearing animals, the best bi-epitopic antibodies are selected for genetic engineering aimed at increasing antigen binding affinity, delaying clearance and improving effector functions. These attributes are essential for clinical application of the bi-epitopic antibody strategy.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. An article of manufacture comprising a packaging material identified for treating cancer, packaging an anti-EGFR antibody comprising the CDR sequences of anti EGFR 111 (CNCM Deposit Number 1-4261) and an anti-EGFR antibody comprising the CDR sequences of anti EGFR 565 (CNCM Deposit Number 1-4262).

2. A pharmaceutical composition comprising as active ingredients an anti-EGFR antibody comprising the CDR sequences of anti EGFR 111 (CNCM Deposit Number I-4261) and an anti-EGFR antibody comprising the CDR sequences of anti EGFR 565 (CNCM Deposit Number I-4262) and a pharmaceutically acceptable carrier or diluent.

* * * * *